US008450092B1

(12) United States Patent
McClune (10) Patent No.: US 8,450,092 B1
(45) Date of Patent: May 28, 2013

(54) PROCESS FOR HARVESTING AND PROCESSING SUGAR-PRODUCING CROPS

(76) Inventor: Lee F. McClune, Knoxville, IA (US)

( * ) Notice: Subject to any disclaimer, the term of this patent is extended or adjusted under 35 U.S.C. 154(b) by 657 days.

(21) Appl. No.: 12/559,175

(22) Filed: Sep. 14, 2009

Related U.S. Application Data (63) Continuation of application No. 11/339,283, filed on Jan. 25, 2006, now abandoned.

(51) Int. Cl.
*C12P 7/02* (2006.01)
(52) U.S. Cl.
USPC .............................. 435/155; 435/161; 127/43
(58) Field of Classification Search
USPC ...................... 435/155, 161; 127/43; 460/123
See application file for complete search history.

(56) References Cited

U.S. PATENT DOCUMENTS

| | | | |
|---|---|---|---|
| 985,440 A | 2/1911 | Needham | |
| 1,425,479 A | 8/1922 | Hobson | |
| 3,093,064 A | 6/1963 | Burner | |
| 3,424,611 A | 1/1969 | Miller | |
| 3,430,584 A | 3/1969 | Bushmeyer | |
| 3,464,856 A | 9/1969 | Smith | |
| 3,485,016 A | 12/1969 | McClellan | |
| 4,057,437 A | 11/1977 | Kracklauer | |
| 4,109,448 A | 8/1978 | Kline | |
| 4,306,940 A * | 12/1981 | Zenty | 202/83 |
| 4,407,111 A | 10/1983 | Brune | |
| 4,613,339 A | 9/1986 | Gunnerman | |
| 6,355,110 B1 | 3/2002 | Donovan | |
| 6,406,546 B1 | 6/2002 | Donovan | |
| 6,406,548 B1 | 6/2002 | Donovan | |
| 6,736,903 B2 | 5/2004 | Minazzoli | |
| 6,807,799 B2 | 10/2004 | Reaux | |
| 6,924,132 B1 * | 8/2005 | Kawasaki et al. ............. 435/161 |
| 2001/0002037 A1 | 5/2001 | Cullinger | |
| 2003/0194302 A1 * | 10/2003 | Hickinbotham .............. 414/432 |

FOREIGN PATENT DOCUMENTS

| | | |
|---|---|---|
| RU | 2062700 | 6/1996 |
| WO | WO 93/16794 | 9/1993 |

OTHER PUBLICATIONS

Defintion of "must" from thefredictionary.com downloaded Jun. 22, 2012.*

* cited by examiner

*Primary Examiner* — Susan Hanley
(74) *Attorney, Agent, or Firm* — Sturm & Fix LLP (57) ABSTRACT

Present-day harvest methods for sweet sorghum are labor intensive, and/or require that large quantities of matter be removed to a central location for processing. A field harvesting process for harvesting and further processing sweet sorghum includes cutting the crop and reducing it to its separated juice and solids in the field. Separation is carried out using a roller press that is water-washed with water removed from the juices in a nanofiltration process. The juice is stored and fermented on the farm, followed by distillation by a mobile distillation process to separate the valuable alcohol from the stillage.

21 Claims, 7 Drawing Sheets

PROCESS FOR HARVESTING AND PROCESSING SUGAR-PRODUCING CROPS

CROSS REFERENCE TO RELATED APPLICATIONS

This application is a Continuation of U.S. application Ser. No. 11/339,283, filed Jan. 25, 2006, entitled IMPROVED PROCESS FOR HARVESTING AND PROCESSING SUGAR-PRODUCING CROPS now abandoned, which is incorporated herein in its entirety. Priority is claimed to all of the patent applications identified in this paragraph.

BACKGROUND OF THE INVENTION

1. Field of the Invention

The present invention relates generally to a method of harvesting and processing sugar-producing crops such as sweet sorghum. More particularly the present invention relates to a process for cutting and processing sweet sorghum in the field to yield its juices, and then to further process the juice via fermentation and distillation to produce ethanol.

2. Background Art

Traditionally, sweet sorghum has been harvested for sorghum syrup production by either cutting and handling the stalks by hand, or by chopping the stalks and blowing the chop into a forage wagon; in either case, the resulting plant matter is carried to a central processing station for the extraction of the juices, cooking and reduction of the juices to sorghum syrup.

The former method requires a large expenditure of manual labor and is typically used in small, such as family sized operations. The juice from the stalks is often squeezed using a single-roller press powered by a horse, mule, or lawn tractor.

The method of chopping the stalks in the field like ensilage is less labor intensive than the previously mentioned method and larger crops may be harvested and processed this way. The drawbacks of this method, however, include: an enormous amount of crop must be transported out of the field to a central processing location, and the resultant organic matter must then be either returned to the field or otherwise disposed of.

Energy is a matter of concern to the country, and will continue to be for some time. Air pollution has improved over the past several decades, but still remains an issue in parts of this country, as well. A recognized partial solution to both the energy and pollution problems is ethanol. Sweet sorghum juice, due to its high sugar content, is an ideal raw material for the production of ethanol. Sweet sorghum has the potential to produce over twice the ethanol per acre as corn, the most common raw material used for ethanol production, today, at significantly less cost. As it stands presently, a more efficient method of harvesting of the sorghum crop must be employed to make the use of this crop for ethanol production feasible.

There is, therefore, a need for a low-labor, efficient process for harvesting and field processing sweet sorghum and extracting the juices for further processing at or near the fields of each producer.

SUMMARY OF THE INVENTION

A purpose of this invention is to provide a process for field harvesting and processing sweet sorghum crops and extracting the juices, as completely as possible, for further processing elsewhere. Another purpose of this invention is to provide a process for fermenting sugar rich substances such as sweet sorghum juice, ultimately for its ethanol. Still another purpose is to provide a portable process for distilling the ethanol from the wine.

A field harvesting process for sweet sorghum is initiated by cutting the stalks of the sweet sorghum close to the ground. The crop is then fed into a multiple roller press, for the extraction of the juices from the cane stalks. The roller press incorporates multiple rollers under high pressure, the crop material passing through the rollers being washed in clean water extracted in a later process to remove a maximum quantity of sugar. A screw press is used to further maximize the sugar extraction from the spent cane stalks or bagasse.

A continuous belt filtering process removes solids from the juices while returning the resulting solid matter for further processing by roller pressing and screw pressing to remove all the potential juices and, subsequently, to be made into a marketable product such as pellets to be used as livestock feed, fuel or other products.

The juices are passed from the continuous belt filter to a nanofilter membrane filtration process where some of the water is removed from the juices to concentrate the sugars in the resulting juice. The water removed is stored in a water tank. Some of the water is used to wash the material passing through the roller press to wash and resaturate the sugars from the solid material, some of the water is used to clean the endless belt filter press, excess water is discharged to the field.

If necessary, the pH of the juices will be adjusted (by the addition of acid) as it travels through the field harvester to reduce bacterial action in the juice. Depending on the operation and desired end product, yeast may be added to the juice within the field harvester as well.

A temporary storage tank, either on board the field harvester or pulled behind or to the side, holds the produced juices. From the field harvester, the juices are transported out of the field to nearby storage and subsequent processing. The juices may be converted to syrup, ethanol, lactic acid or other products.

The present invention includes a fermentation process, which takes place within the storage units in a matter of days, and a portable distillation process to recover the ethanol from the resultant wine and to concentrate this ethanol to fuel ethanol. Tanks for storage and fermentation may take many forms. Stationary, rigid tanks may be used, but portable bladders provide a less expensive and more flexible alternative. In either case, a vent for permitting the release of Carbon Dioxide ($CO_2$) gas is necessary during the fermentation process.

A portable distillation process, mounted on a "low-boy" type truck or semi trailer, concentrates the ethanol to a fuel level. The distillation process may use fossil fuel(s) for the heat required, but an aspect of the present invention is to gasify the solid crop material or bagasse for the heat needed for distillation.

A distillation process comprises:
 a heating unit in which the fermented juices (wine) are heated so the alcohol will evaporate at about 180° F.;
 a condensing unit in which the alcohol is cooled so it condenses; and
 a molecular sieve unit in which distilled alcohol is concentrated to fuel grade.

Strict quality control measures must be taken at this point in the overall process due to the requirement that the alcohol be of fuel grade.

The novel features which are believed to be characteristic of this invention, both as to its organization and method of operation together with further objectives and advantages thereto, will be better understood from the following description considered in connection with accompanying drawings in which a presently preferred embodiment of the invention is illustrated by way of example. It is to be expressly understood however, that the drawings are for the purpose of illustration and description only and not intended as a definition of the limits of the invention.

BEST MODE FOR CARRYING OUT THE INVENTION

Figure 1:
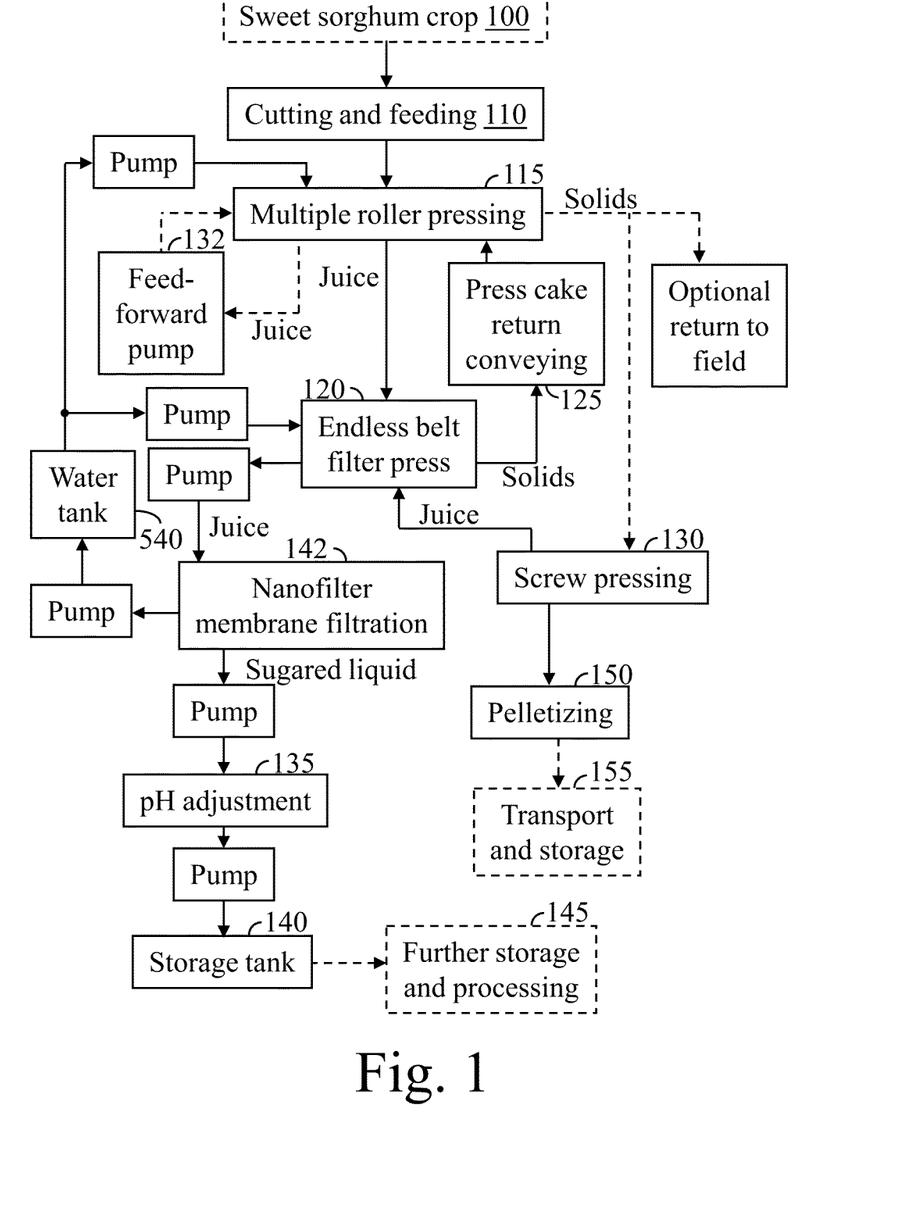
FIG. 1 shows a flow diagram of a sweet sorghum field harvesting process.

A flow diagram for a mobile sweet sorghum field harvesting process is shown in FIG. 1. At the top, the sweet sorghum crop 100, mature for harvest, is harvested by a field harvester 580 (see FIG. 5). The cutting and feeding step 110 implies cutting the crop off near the ground and feeding it into a pressing process 115 (a multiple roller press) for the primary step in separating the juices from the solids. The extracted juices are passed to an endless belt filter press process 120, where the solids are strained out of the juice. From the endless belt filter press process 120, a filter cake is obtained and returned via a conveyance 125 that returns the cake to the multiple roller pressing process 115 for additional juice extraction. The solids (bagasse) from the multiple roller pressing process 115 may be:

1. expelled back to the field;
2. passed to a screw press process 130 where the last of the available juice to be extracted is removed; or
3. a combination of 1 and 2.

The juices from the latter stages of the multiple roller pressing process 115 are cycled forward at each stage of the multiple roller pressing process 115 by feed-forward pumps 132 to wash and help extract more of the sugars from the solids. The cleaned and filtered juices are then pumped from the endless belt filter press process 120 to an on-board nanofiltration membrane process 142 for partial removal of excess water and consequent increased concentration of the sugars. The water removed in the nanofiltration membrane process 142 is used as wash water for the roller pressing process 115, belt filter wash water, and to replenish the wash tank 540. Pumps may be used to transport the water in each of the wash activities. Excess water is expelled to the field. Eventually, all the juices pass to an optional pH adjustment 135 where the pH is measured and adjusted to about 4.5-4.8 to inhibit bacterial action. If the final product is to be lactic acid or some other products, this step may be unnecessary.

The juices then continue to an on-board or trail-behind storage tank 140 for temporary storage until the juices are removed and transported to nearby larger storage/fermentation tanks for fermentation and subsequent distillation in a final processing step 145.

Simultaneously, the solids leaving the screw press process 130 may be made into pellets in a rotary ring pelletizing process 150 and transported to storage 155. These pellets may be used for fuel for alcohol distillation, for livestock feed or for other purposes. The solids may instead be converted into other, marketable products.

Figure 2A:
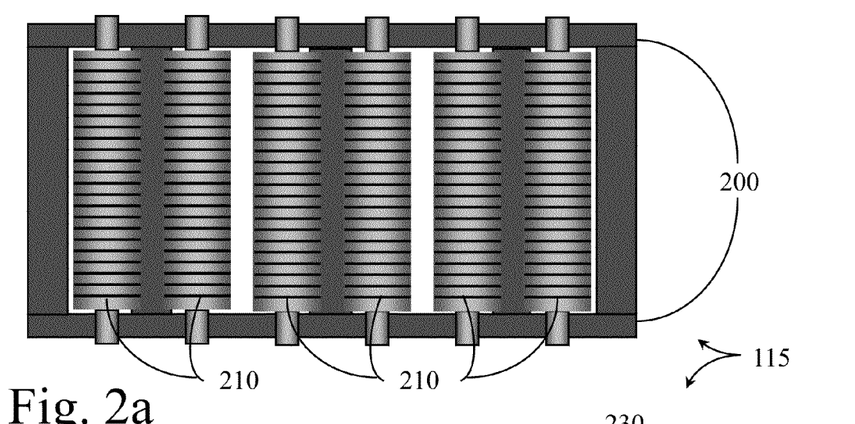
FIG. 2a is a plan view of a roller press unit for removal of sugar-laden juice from cane stalk.
Figure 2B:
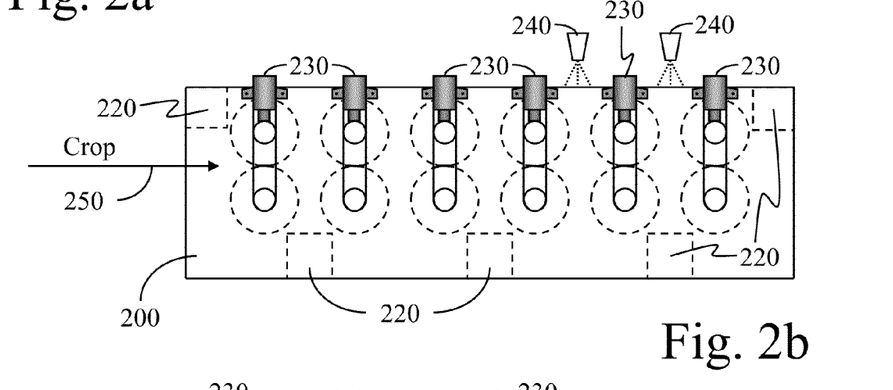
FIG. 2b is a side elevation view of a roller press unit for removal of sugar-laden juice from cane stalk.
Figure 2C:
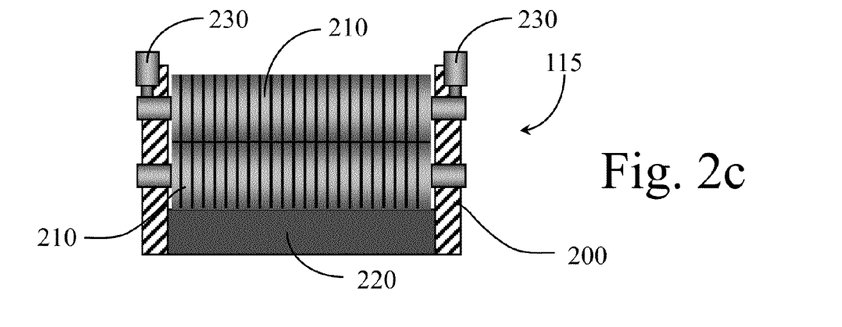
FIG. 2c is a frontal elevation view of a roller press unit for removal of sugar-laden juice from cane stalk.

The physical unit for the multiple roller press process 115 is shown in FIG. 2. The heavy side rails 200 of the frame support multiple rollers 210 whose purpose is to squeeze the juice from the stalks of the crop. The rollers 210 have optional grooves machined into them and are hung on double roller bearings at each end. Spacing between the side rails 200 is maintained by tie beams 220. Force is applied downward to each roller in the top layer of rollers 210 by hydraulic cylinders 230.

At one or more locations in the roller press, the crop material is sprayed with clean water through nozzles 240 from the water tank 540 (FIGS. 1 and 5) to help extract all the sugars from the solid crop material. In the preferred embodiment, the locations of the water spray nozzles 240 would be in the vicinity of the last rollers through which the crop material passes. The direction of travel of the crop material is shown in FIG. 2b by an arrow 250.

Figure 3A:
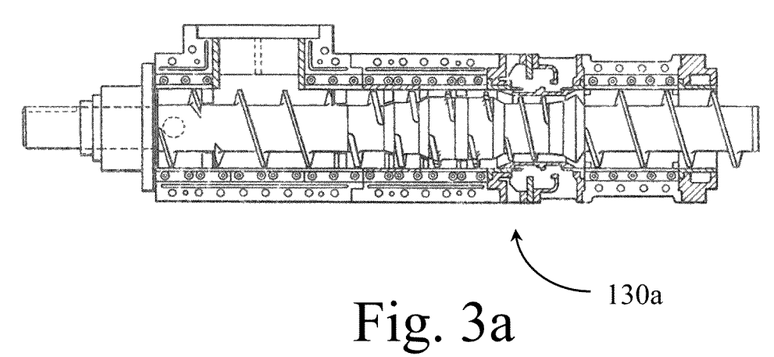
FIG. 3a shows a single screw press for further removal of sugar-laden juice from cane stalk.
Figure 3B:
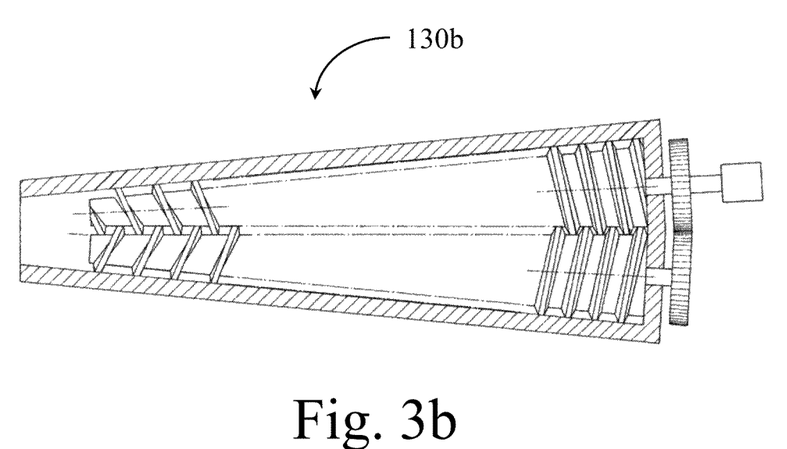
FIG. 3b shows a double screw press for further removal of sugar-laden juice from cane stalk.

A screw press unit for the screw pressing process 130 is used to maximize the production of juice from the sweet sorghum crop. Typical examples are shown in FIG. 3, but this invention is not limited to any particular design of screw press unit. In FIG. 3a a single screw press extruder 130a is shown, while in FIG. 3b a double screw press 130b is shown.

Figure 4:
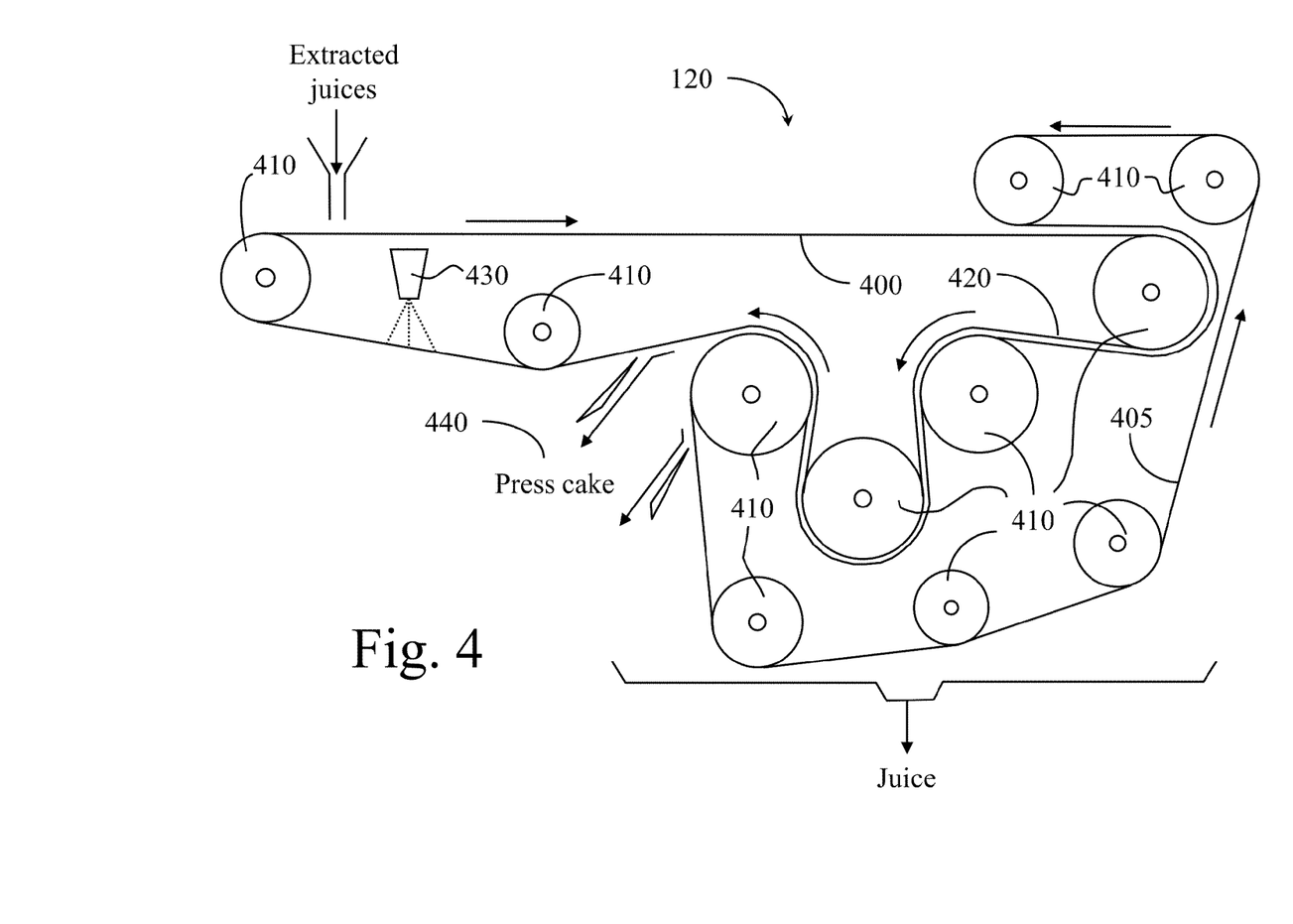
FIG. 4 shows an endless belt filter press unit.

From the multiple roller pressing process 115 and the screw pressing process 130, the extracted juices with entrained solids (slurry) pass to the endless belt filter press process 120 shown in FIG. 4. Again, the present invention is not limited to a particular endless belt filter unit design. As the name implies, the endless belt filter press unit comprises two endless belts 400, 405 routed around a series of rollers 410. The belts run close to one another over part of their length 420 to compress and remove the entrained solids from the juices. This compression accomplishes two effects:

1. The squeezing of much of the juice from the solids.
2. The forming of a press cake 440 to be returned to the multiple roller press unit 115 for further juice extraction.

This press cake 440 is conveyed back to the multiple roller press 115 by the press cake return conveyor 125, where more of the juice is pressed out of the solids.

A water nozzle 430 sprays the filter belt 400 with water from the water tank 540 (FIGS. 1 and 5) to clean the belt so it can be used continually during the harvest session without requiring periodic cleaning.

Figure 5:
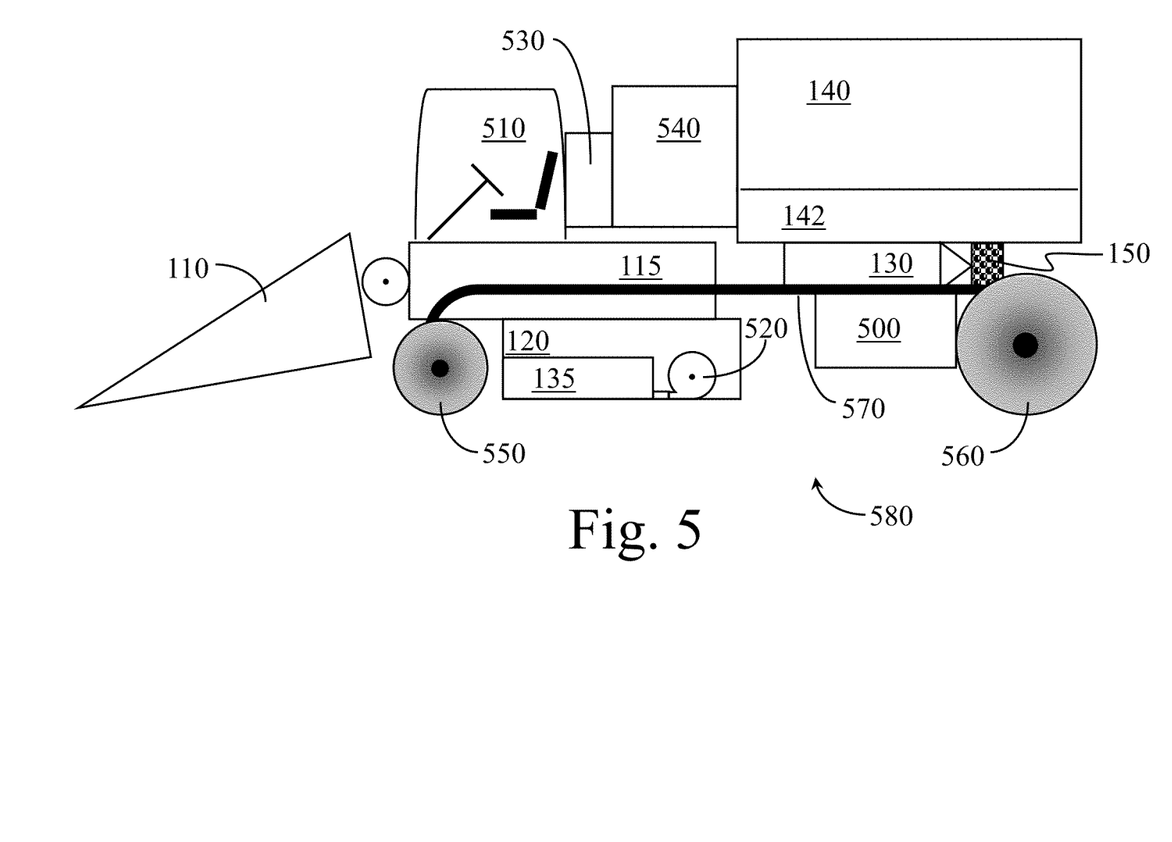
FIG. 5 shows a layout of a sweet sorghum harvester.

An example of how a sweet sorghum field harvester 580 may be laid out is shown in FIG. 5. The field harvester 580 is powered by an engine 500, preferably diesel. The harvester is operated from a cab 510. The cutting and feeding unit 110 is carried on the front of the field harvester 580 where the crop is sheared from the ground and transferred to the multiple roller press process 115 near the cab 510. The endless belt filter press process 120 is beneath the multiple roller press 115. Feed-forward pumps 132 are close to the multiple roller press unit. Transfer and wash pumps 520 are in close association with the endless belt filter press process 120 as it transfers the clean juice from the endless belt filter press process 120 to the nanofiltration membrane process 142. From there, a pH adjustment of the juices is carried out, if necessary before or as the juices are pumped to the storage tank 140. A tank for acid 530 for adjusting the pH of the juice to about 4.5-4.8 is carried in front of a water tank 540. Yeast may also be introduced on board the harvester 580. Water, for washing the endless belt 400, is contained in a tank 540.

The solids, or bagasse, continue from the multiple roller press process 115 to the screw press process 130, and then, optionally, to a pelletizing process 150 to form them into pellets useful for feed, fuel or other products.

The sweet sorghum field harvester 580 need not be a self-propelled machine as indicated in FIG. 5. A sweet sorghum field harvester 580 that is made to be pulled behind a tractor or other vehicle, and powered via a power takeoff shaft or other means is a viable alternative and may be attractive for smaller operations. In any case, the sweet sorghum field harvester is mobile, that is, not stationary.

The field harvesting process described above may be used for any sugar-containing crop including sweet sorghum and sugar cane.

Figure 6:
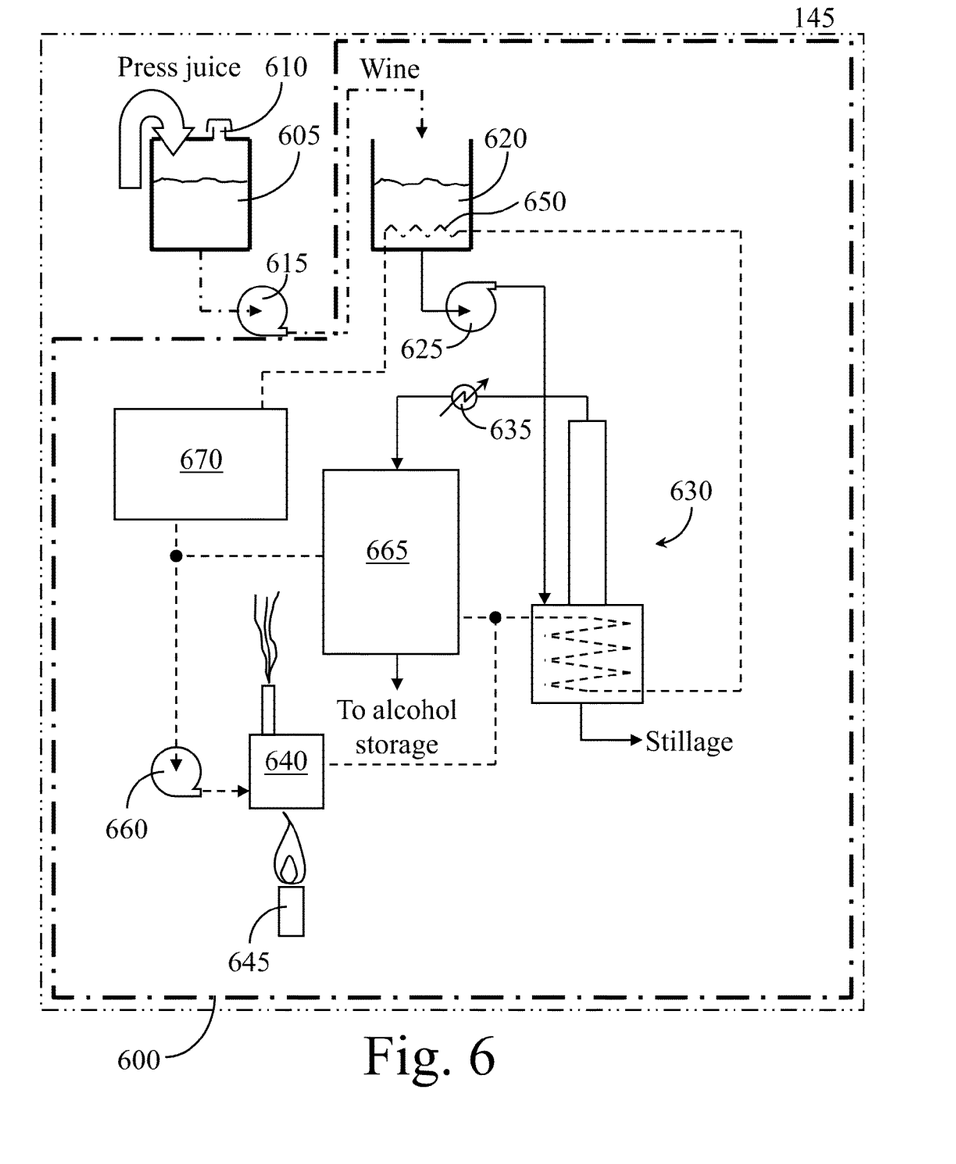
FIG. 6 shows a typical distillation process.
Figure 7:
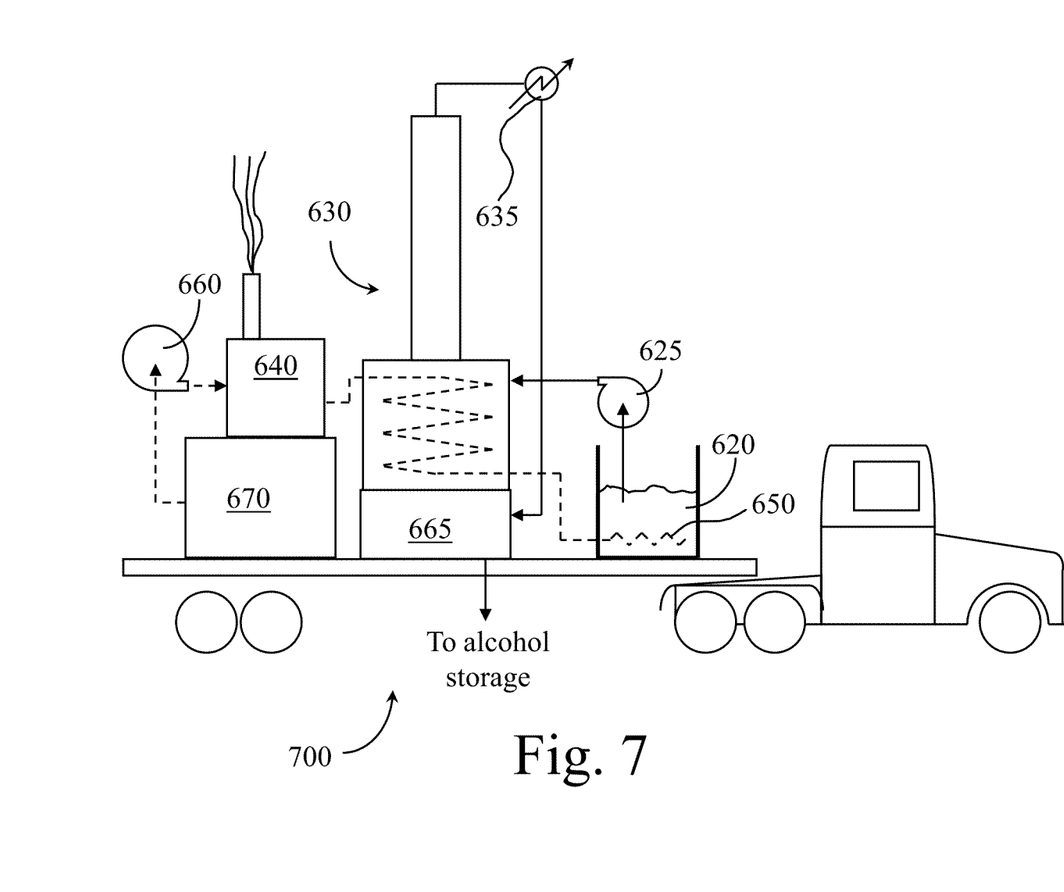
FIG. 7 shows the distillation process unit mounted on a semi-trailer.

After the sweet sorghum crop has been processed into its juices in the sweet sorghum field harvester 580, the juices must be further processed into a useable and saleable product. Thus, other aspects to the present invention are further storage and processing 145 comprising:
1. fermentation tanks 605 as shown in FIG. 6; and
2. a portable distilling process 700 as illustrated in FIG. 7.

Thus, sweet sorghum juices from the field harvester 580 are transferred into storage/fermentation tanks 605. During this transfer from the field harvester 580 the selected yeasts are added, and the fermentation process begins and typically lasts for a few days. Throughout fermentation, $CO_2$ is produced. These fermentation tanks 605 may take many forms. A rigid, stationary tank would be suitable, however, a portable, fiber elastic bladder would be less expensive and more flexible. Irrespective of the form of the storage/fermentation tanks 605, it must have a vent 610 for venting the $CO_2$ produced by the yeast during fermentation. The $CO_2$ may be captured for sale.

The ethanol laden juices, called wine are transported or transferred from the storage/fermentation tanks 605 under gravity or with a wine pump 615 into a wine tank 620. From the wine tank 620, the wine is transported under gravity or by a distillation pump 625 into a distillation boiler/column 630. In the distillation column 630, the alcohol is separated from the remainder of the wine, or stillage. The resulting low-grade alcohol may be further cooled in a heat exchanger 635 used to preheat the wine before being further refined in a molecular sieve stripping unit 665. This final product fuel ethanol is then loaded into a tank for storage or transport.

Heat for the distillation column is provided by heating water in a boiler 640. The fuel 645 for the boiler may be Liquid Propane (LP), or other fossil fuel, or the bagasse (the solids left over after removing the juice from the sweet sorghum) may be put through the process of gasification, and the resulting fuel 645 burnt to heat the boiler 640. The heat from the bagasse burning can also be used in the distillation process.

Gasification of a carbonaceous material such as bagasse results in a fuel referred to as producer gas. The combustible components are, largely, carbon monoxide (CO) and hydrogen ($H_2$).

Steam, from the boiler 640, first travels to the distillation column 630. From the distillation column 630, the condensate is used in the line from the wine tank 620 to preheat the wine before distillation. A wine tank heat exchanger 650 in the wine tank 620 imparts the heat to the wine. From the wine tank 620, the condensate moves to a condensate holding tank 670. The condensate is finally returned to the boiler through a boiler feed pump 660. A heat transfer fluid may also be used, instead of steam, to transfer heat for the distillation process.

FIG. 7 depicts an example of a portable part of the distillation process 600 (also inside the heavy dot-dashed line in FIG. 6). In this case, the distillation column 630, with its heat exchanger 635, the boiler 640, condensate holding tank 670, the wine tank 620, the molecular sieve stripping unit 665, associated pumps 615, 625, the boiler feed pump 660, and associated controls are carried on a semi trailer 700. Other combinations are possible.

The above embodiments are the preferred embodiments, but this invention is not limited thereto. Many of the elements of the process mentioned, above, are optional, providing for a large degree of flexibility and pricing. It is, therefore, apparent that many modifications and variations of the present invention are possible in light of the above teachings. It is, therefore, to be understood that within the scope of the appended claims, the invention may be practiced otherwise than as specifically described.

I claim:

1. A method for harvesting and processing sugar-containing crops growing in ground in a field with a mobile field harvester, the method comprising:
    (a) cutting the sugar-containing crop close to the ground, but above the ground, near a base of said sugar-containing crop;
    (b) feeding the sugar-containing crop into a roller press in a mobile field harvester;
    (c) extracting juices from a solid component of the sugar-containing crop in the roller press within the mobile field harvester;
    (d) using a forward feed pump operatively attached to the mobile field harvester to pump at least some of the juices extracted from the roller press back into the roller press for helping to moisten the solid component of the sugar containing crop;
    (e) adding water to the sugar-containing crop to further moisten the solid component of the sugar containing crop as it passes through the roller press wherein the step of adding water to the sugar-containing crop comprises:
        (i) extracting excess water from the juices from step (c) using a nanofilter membrane process with a nanofilter operatively attached to the mobile field harvester for the purpose of creating an on board water supply; and
        (ii) using the on board water supply from the nanofilter membrane process to saturate the sugar-containing crop with water from the water supply in at least one location in the roller press; and
    (f) using the juices to make ethanol using at least one portable fermentation container located at or close to the field where the sugar containing crop was grown and harvested.

2. The method of claim 1 further comprising after step (e) and before step (f) the additional step of:
    extracting juice from the solid component of the sugar-containing crop in a screw press within the mobile field harvester.

3. The method of claim 2 additionally comprising filtering any solid component from the juice of the sugar-containing crop with an endless belt filter contained within the mobile field harvester.

4. The method of claim 2 additionally comprising adjusting the pH to reduce the pH of the juice to inhibit bacterial action.

5. The method of claim 4 additionally comprising measuring the pH to control the pH reduction.

6. The method of claim 4 additionally comprising pelletizing remaining solid component from the extraction to produce pellets wherein a pelletizer is attached to the mobile field harvester for the pelletizing.

7. The method of claim 2 wherein the sugar-containing crop is sweet sorghum.

8. The method of claim 2 wherein the sugar-containing crop is sugar cane.

9. The method of claim 1 further comprising after step (c) and before step (d) the additional step of:
   filtering the solid components from the juices of the sugar-containing crop with an endless belt filter press unit containing with the mobile field harvester.

10. The method of claim 1 additionally comprising adjusting the pH to reduce the pH of the juice to inhibit bacterial action.

11. The method of claim 10 additionally comprising measuring the pH to control the pH adjustment.

12. The method of claim 1 additionally comprising converting the solid component of the sugar-containing crop to pellets by attaching a pelletizer to the mobile field harvester so the pellets can be made at the same time that the juice is being harvested.

13. The method of claim 1 wherein the sugar-containing crop is sweet sorghum.

14. The method of claim 1 wherein the sugar-containing crop is sugar cane.

15. The method of claim 1 wherein the step of using the juices to make ethanol further comprises:
   (a) fermenting the juice from the sugar-containing crop;
   (b) providing a source of heat for distillation; and
   (c) distilling the fermented juice in a mobile distillation column.

16. The method of claim 15 wherein fermentation occurs in at least one portable fermentation elastic bladder.

17. The method of claim 15 wherein a source of heat for distillation comes from bagasse from the sugar-containing crop.

18. The method of claim 17 wherein the bagasse is used to produce steam that is used as the source of heat for distillation.

19. The method of claim 18 wherein excess heat is used to preheat the juice before distillation.

20. The method of claim 18 wherein excess heat from condensing and cooling the ethanol is used to preheat the juice.

21. The method of claim 15 wherein the mobile distillation column is moved to a location at or close to the field where the sugar containing crop was grown and harvested and wherein juices from the at least one portable fermentation container is transferred to the mobile distillation column.

* * * * *